United States Patent [19]

Chiesi et al.

[11] Patent Number: 5,708,144
[45] Date of Patent: Jan. 13, 1998

[54] PROCESS FOR THE PURIFICATION OF NATURAL PULMONARY SURFACTANT MATERIAL USING SUPERCRITICAL FLUIDS

[75] Inventors: Paolo Chiesi; Paolo Ventura; Roberto Pighi; Vittorino Servadio; Walter Recchia, all of Parma, Italy

[73] Assignee: Chiesi Farmaceutici S.p.A., Parma, Italy

[21] Appl. No.: 424,503

[22] PCT Filed: Nov. 19, 1993

[86] PCT No.: PCT/EP93/03239

§ 371 Date: May 22, 1995

§ 102(e) Date: May 22, 1995

[87] PCT Pub. No.: WO94/12525

PCT Pub. Date: Jun. 9, 1994

[30] Foreign Application Priority Data

Nov. 27, 1992 [IT] Italy .................... MI92A2718

[51] Int. Cl.$^6$ .................... C07K 14/00; A61K 35/42
[52] U.S. Cl. .................... 530/359; 530/422; 530/426; 530/427; 424/520; 424/557; 514/975
[58] Field of Search .................... 530/359, 422, 530/426, 427; 424/520, 557; 514/975

[56] References Cited

U.S. PATENT DOCUMENTS

| | | | |
|---|---|---|---|
| 4,749,522 | 6/1988 | Kamarei | 260/412.8 |
| 4,776,173 | 10/1988 | Kamarei et al. | 62/63 |
| 5,024,995 | 6/1991 | Robertson et al. | 514/21 |

*Primary Examiner*—Cecilia J. Tsang
*Assistant Examiner*—Abdel A. Mohamed
*Attorney, Agent, or Firm*—Oblon, Spivak, McClelland, Maier & Neustadt, P.C.

[57] ABSTRACT

A process for purifying natural pulmonary surfactant by dispersing animal lung tissue on an inert carrier and extracting with a supercritical fluid.

12 Claims, No Drawings

PROCESS FOR THE PURIFICATION OF NATURAL PULMONARY SURFACTANT MATERIAL USING SUPERCRITICAL FLUIDS

BACKGROUND OF THE INVENTION

The present invention relates to a process for the purification of animal pulmonary surfactant by means of extraction and separation of undesired components consisting of lipidic substances of a low polar power.

DESCRIPTION OF THE BACKGROUND

Pulmonary surfactant (PS) is a vital material, coating the surface of pulmonary alveoli, which acts reducing the surface tension at the air-liquid interface, thus stabilizing alveoli and preventing them from collapsing during respiration.

Lack of PS causes a severe respiratory disease named respiratory distress, which is the cause of high morbidity and mortality, particularly in pre-term infants and in adults affected by various pathologies involving a severe pulmonary insufficiency.

The effectiveness of a substitutive therapy based on the instillation of exogenous pulmonary surfactant material in lungs has already been widely proved.

Natural surfactants and pharmaceutical compositions for the use thereof in respiratory distress have been disclosed in a number of patents: GB 2,050,832, U.S. Pat. No. 4,397,839 and EP 0,119,056 (Tokyo Tanabe); EP 0,145,005 (Veb Arzneimittel Dresden); EP 0,286,011 (Chiesi).

All of the processes for the preparation of surfactant material starting from animal lungs disclosed in said patents are substantially based on an extraction step, characterized by a number of washing, centrifugation and extraction operations, with suitable organic solvents, and a subsequent purification step in order to separate the active fraction and remove impurities as well as undesired inactive components.

The purification step is of paramount importance in obtaining an active material having a well-defined, reproducible composition.

Natural PS is a complex lipoprotein mainly consisting of phospholipids and specific proteins.

Phospholipids, particularly phosphatidylcholine (PC), its disaturated form dipalmitoyl phosphatidylcholine (DPPC) and phosphatidylglycerol play an essential role in the physiological function of natural surfactant in reducing the surface tension in alveoli.

Specific apoproteins of surfactant, identified as SP-B and SP-C, are also vital for the biological action of natural surfactant, since they promote surfactant adsorption and distribution on the lung surface.

Surfactant disclosed in GB 2,050,832 and in U.S. Pat. No. 4,397,839 is subjected to a series of dialysis, centrifugation, washing, filtration, drying (or freeze-drying) procedures in order to remove impurities and the neutral lipids and cholesterol excesses.

Nevertheless, the resulting active material has a widely variable composition, in fact the inventors: themselves, in the subsequent EP Patent 0,119,056, make use of a semi-synthetic preparation consisting of a natural lipoprotein, extracted from mammal lung, mixed with phospholipids and synthetic fatty acids, in order to obtain a better composition.

Surfactant disclosed in EP 0,145,005 is purified by extraction with a water-insoluble alcohol and subsequent separation from the fraction which is insoluble in said alcohol. However, an active material is obtained having a very low content in phospholipids, which are present in a ratio of 40-70% by weight.

On the contrary, surfactant disclosed in EP 0,286,011, which is of a completely natural origin, has a satisfactory composition characterized by a high polar lipid content and substantially free from such inactive components as carbohydrates, neutral lipids and cholesterol. In this case, the purification of the crude surfactant material is carried out by elution through a column of Lipidex®, a particularly hydrophobic resin which is specifically suitable for the separation of polar lipids. However this purification method, although proving to be highly effective, suffers from a series of drawbacks industrial scale, above all the use of large amounts of chlorinated solvents.

The extraction with supercritical fluid provides an effective alternative method for the purification of natural substances.

Supercritical fluids are substances which in ambient conditions behave as gas, whereas at temperatures and pressures higher than the critical Temperature (cT) and the critical Pressure (cP) are in the liquid state.

The first examples of the use of the extraction with supercritical fluids relate to extraction of hop, the decaffeinization of coffee, the extraction of nicotine from tobacco, the fractioning of oils and fats, the extraction of essential oils used both in, perfumes and as flavours, the extraction of vegetable oils of various type. U.S. Pat. No. 4,776,173 describes a method for obtaining animal or plant derived materials by means of cryogrinding tissues and organs allowing fracture of materials into small particles and disrupting membranes of tissues, organs, and cells, in order to release desired biomolecules in the extraction medium.

PCT Application 87/02697 discloses a process for the extraction of animal material components by the use of supercritical fluids. The process consists in contacting homogenates of animal tissues or organs with the supercritical fluid, thereafter carrying out the extraction under specific operative conditions.

However, the use of said process in the purification of a complex lipoprotein such as PS, which is physically organized in the form of lamellar bodies or tubular myelin, turned out to be ineffective.

SUMMARY OF THE INVENTION

Now it has been found, and it is the object of the present invention, that the procedure with supercritical fluids can advantageously be used for the purification of PS if the extractive step is preceded by dispersing the material on a high surface area inert solid, to increase as much as possible the surface area of the material to extract, therefore promoting the permeation of the material itself with the solvent, increasing its extractive power.

Therefore, one of the object's of the invention is provided by an improved process for the purification of natural PS.

A further object of the invention is the use of supercritical fluids for the extraction of materials which are components of animal tissues or organs, which process is characterised in that the starting material is previously dispersed on an inert carrier material in order to promote the extraction.

DETAILED DESCRIPTION OF THE INVENTION

The supercritical fluid is preferably carbon dioxide, since it is non toxic, non flammable, non corrosive, it has a low critical temperature (31.06° C.), a high volatility under low pressure and can easily be recovered from the solute of the supercritical phase. Moreover, carbon dioxide is markedly apolar, which, in the case of the use with allows to avoid the extraction of highly polar products such as sugars, glycosides, inorganic salts, amino acids and aromatic substances.

Furthermore, the low cost, the easiness of achievement and the lack of aggressivity against proteins make it an optimum extraction solvent.

It should also be evidenced that, in the extraction with carbon dioxide, mechanical energy is used to separate the solvent from the extract, instead of thermal energy, which is the case with conventional techniques, therefore improving the thermodynamic yield of the system.

The supercritical region is the area in which the extraction process takes place. In this area, the gas cannot be liquefied due to its pressure; moreover, in this state, carbon anhydride can be liquefied by cooling, thus avoiding condensation.

The use of the supercritical fluid technique in the process for the purification of PS involves remarkable advantages:
1. achievement of a product which is substantially free from residual solvents;
2. drastic reduction of chlorinated and non chlorinated solvents, which are present in the process in very low amounts only in the separation of surfactant from the inert carrier, in fact, the amount of solvent used in the present invention is from about 30 to about 50 ml per gram of Purified product, whereas the process disclosed in EPO 286011 uses about 600 ml per gram of purified product;
3. cut in the costs of the purification plant.

As an inert carrier to disperse the material to be extracted, glass beads of a suitable size Extrelut® (diatomaceous earth), Celite® (diatomaceous earth) and the like can be used. Celite® is preferred for both the good yield and the low cost.

The weight ratio of inert material to material to extract ranges between 0.5:1 to 3:1, 1:1 being preferred.

The extraction is carried out at temperatures from 35° C. to 55° C., preferably at 40° C., under pressures from 180 to 300 atmospheres, preferably 200, for a time varying from 3 to 9 hours, preferably 7 hours.

In a preferred embodiment of the invention, the extraction step is subdivided in two cycles, evaporating to dryness the material from the first extraction cycle and subjecting the resulting powder to a second extraction cycle. Said procedure involves a better extraction of low polar substances.

The following examples evidence the optimum operative conditions to obtain the best extraction performances.

In the examples, only supercritical $CO_2$ was used, however, other supercritical fluids or possible combinations of supercritical fluids can obviously be used optionally in the presence of a cosolvent, is understood by those skilled in the art.

The extraction plant is not critical to the purposes of the present invention, since the conventional plants operating with supercritical fluids can be used.

Any changes in the configuration and parameters the used plant can be carried out by those skilled in the art, without departing from the spirit and scope of the invention.

The crude paste used in the examples was obtained according to the procedure disclosed in EP 0, 286,011.

EXAMPLE 1

30 g of PS crude paste are dissolved in 200 ml of chloroform at room temperature, with stirring. When the dissolution is complete, 30 g of Celite 545 (Merck 2693) are added in a 1:1 w/w ratio. The solvent is evaporated to dryness under vacuum at 35° C. A powder is obtained, partly conglomerated in granules, which is placed into the plant extractor. An extraction cycle is carried out under the following conditions:

| fluid | carbon dioxide |
|---|---|
| pressure | 200 bars |
| extractor temperature | 40° C. |
| separator temperature | 34° C. |

The cycle lasts about 3 hours, then the mixture is removed from the extractor and suspended in 500 ml of chloroform. The suspension is stirred for 5 min. and the solvent is evaporated to dryness at 35° C. The obtained powder is loaded again into the plant extractor and an extraction cycle is repeated, under the same conditions, for about 3 hours.

Finally the mixture is removed from the extractor, suspended in 500 ml of chloroform, stirring for 10 min. at room temperature, and filtered with suction. The resulting clear chloroform solution is evaporated to dryness under vacuum at 35° C., to obtain 24 g of a surfactant purified paste.

The separator is washed twice with 150 ml of chloroform, the two washings are combined and evaporated under vacuum at 35° C. 5.2 g of impurities are obtained.

EXAMPLE 2

Similar results can be obtained following the procedures described in example 1, without resuspending the material in chloroform half way through the cycle.

In this case, the mixture from the extractor is mixed by hand and loaded again, to repeat the extraction cycle under the same operative conditions.

EXAMPLE 3

Following the same procedure as in examples 1 and 2, but carrying out the extraction cycle under a pressure of 250 bars, 23.5 g of purified surfactant paste were obtained from 30 g of the starting PS crude paste, separating 6.5 g of impurities.

EXAMPLE 4

30 g of PS crude paste are dissolved in 400 ml of chloroform at room temperature, with stirring. When the dissolution is complete, 60 g of Celite 545 (Merck 2693) are added in a 2:1 w/w ratio. The solvent is evaporated to dryness under vacuum at 35° C. A powder is obtained which is placed into the plant extractor.

An operative cycle is carried out under the following conditions:

| fluid | carbon dioxide |
|---|---|
| pressure | 200 bars |
| extractor temperature | 40° C. |
| separator temperature | 34° C. |

The cycle lasts about 3 hours 30 min., then the mixture is removed from the extractor and suspended in 500 ml of chloroform. The suspension is stirred for 5 min. and the solvent is evaporated to dryness at 35° C. The obtained powder is loaded again into the plant extractor and an extraction cycle is repeated, under the same conditions, for about another 3 hours 30 min.

Finally the mixture is removed from the extractor, suspended in 500 ml of chloroform, stirring for 10 min. at room temperature, and filtered with suction. The filtered solid is resuspended in 500 ml of chloroform and filtered with suction again.

The two chloroform solutions obtained are evaporated to dryness under vacuum at 35° C., to obtain 23.7 g of a surfactant purified paste.

The separator is washed twice with 150 ml of chloroform, the two washings are combined and evaporated under vacuum at 35° C. 5.0 g of impurities are obtained.

To stress the importance of the dispersion step of the material to extract on an inert carrier, as well as that of the general operative conditions, an example of a preparation carried out according to the prior art teachings is also reported.

EXAMPLE 5

30 g of PS crude paste are placed into the plant extractor.

An extraction cycle is carried out under the following conditions:

| fluid | carbon dioxide |
|---|---|
| pressure | 200 bars |
| extractor temperature | 40° C. |
| separator temperature | 34° C. |

The cycle lasts 7 hours, then the extractor is unloaded and washed with 600 ml of chloroform.

The paste is combined with the chloroform and the suspension is stirred to complete dissolution. The solution is evaporated to dryness at 35° C. under vacuum, to obtain 28.5 g of purified paste.

The separator is washed twice with 150 ml chloroform, the two washings are combined and evaporated under vacuum at 35° C., to obtain 1.2 g of impurities.

The PS preparations obtained according to the above examples were analyzed against a control sample, i.e. a preparation obtained according to the purification procedure disclosed in EP 0,286,011 (Lipidex® column). The preparation of examples 1-4 evidenced a cholesterol and triglycerides content meeting the quality requirements; moreover, compared with the control sample, said preparations had a content in residual solvents lower than that of the control sample.

On the contrary, the preparation of example 5 showed an analytical profile not meeting the required parameters. This proves the criticality of the predispersion of the material to be extracted on the inert carrier, which is characteristic of the process of the invention.

More particularly, in the following Table the analytical data of PS samples obtained according to the invention (examples 1 and 4), to example 5 (no pre-dispersion) and EP 0,286,011 (control) are reported.

TABLE 1

Determination of the percent content in total phosphorous (as an index of the phospholipids content), proteins, cholesterol and triglycerides in PS samples.

| % Content | Example 1 | Example 4 | Example 5 | Control |
|---|---|---|---|---|
| Phosphorous | 3.79 | 3.84 | 2.75 | 3.6–4.0 |
| Proteins | 1.53 | 1.24 | 1.32 | 0.5–1.5 |
| Cholesterol | 0.47 | 0.40 | 9.23 | ~1% |
| Triglycerides | 0.52 | 0.6 | 6.85 | ~1% |

The PS purified paste obtained according to examples 1 and 4 of the invention was resuspended in physiological saline at a concentration of 80 mg of phospholipids/ml and subjected to an evaluation of the effects on the pulmonary mechanics of foetuses of prematurely born rabbits, according to the procedure described by Robertson B. and Lachmann B. in Experimental Lung Research 14: 279–310, 1988, to verify that the novel purification procedure does not affect the biological properties in any way.

The results obtained in the animal confirmed the effectiveness of said preparations, which proved to have the same activity degree as the one of the product obtained by the column purification procedure.

We claim:

1. A process for extracting natural pulmonary surfactant from an animal lung tissue, comprising the steps of:

dispersing said animal lung tissue on an inert carrier material, and extracting said animal lung tissue with a supercritical fluid.

2. The process of claim 1, wherein said animal lung tissue material is in the form of a paste.

3. The process of claim 1, wherein said supercritical fluid is carbon dioxide.

4. The process of claim 1, where said inert carrier material is glass beads or diatomaceous earth.

5. The process of claim 1, comprising a plurality of said extracting steps.

6. A natural pulmonary surfactant obtained by the process of claim 1.

7. The process of claim 1, wherein the weight ratio of inert carrier material to animal lung tissue material ranges from 0.5:1 to 3:1.

8. The process of claim 7, wherein said ratio is 1:1.

9. The process of claim 1, wherein said extracting step is carried out at a temperature of 35° to 55° C. under a pressure from 180 to 300 atmospheres and for a time from 3 to 9 hours.

10. The process of claim 9, wherein said extracting step is carried out at a temperature of 40° C. under a pressure of 200 atmospheres, and for a time of 7 hours.

11. The process of claim 1, wherein said extracting step comprises extracting with a mixture of said supercritical fluid and a cosolvent.

12. The process of claim 11, wherein said cosolvent is chloroform.

* * * * *